United States Patent
O'Hara et al.

(10) Patent No.: US 12,042,506 B2
(45) Date of Patent: Jul. 23, 2024

(54) PREBIOTIC COMPOSITIONS AND METHODS OF PRODUCTION THEREOF

(71) Applicant: Optibiotix Limited, York (GB)

(72) Inventors: Stephen Patrick O'Hara, York (GB); Oswaldo Hernandez, York (GB); Sofia Kolida, York (GB)

(73) Assignee: OPTIBIOTIX LIMITED (GB)

(*) Notice: Subject to any disclaimer, the term of this patent is extended or adjusted under 35 U.S.C. 154(b) by 437 days.

(21) Appl. No.: 17/044,946

(22) PCT Filed: Apr. 4, 2019

(86) PCT No.: PCT/GB2019/050994
§ 371 (c)(1),
(2) Date: Oct. 2, 2020

(87) PCT Pub. No.: WO2019/193357
PCT Pub. Date: Oct. 10, 2019

(65) Prior Publication Data
US 2021/0161923 A1 Jun. 3, 2021

(30) Foreign Application Priority Data
Apr. 4, 2018 (GB) .................................. 1805577.2

(51) Int. Cl.
| | | |
|---|---|---|
| A61K 31/702 | (2006.01) |
| A23L 27/30 | (2016.01) |
| A23L 33/21 | (2016.01) |
| A61K 9/14 | (2006.01) |
| A61P 1/00 | (2006.01) |

(52) U.S. Cl.
CPC ............ *A61K 31/702* (2013.01); *A23L 27/30* (2016.08); *A23L 33/21* (2016.08); *A61K 9/14* (2013.01); *A61P 1/00* (2018.01); *A23V 2002/00* (2013.01)

(58) Field of Classification Search
None
See application file for complete search history.

(56) References Cited

U.S. PATENT DOCUMENTS

| | | | |
|---|---|---|---|
| 2007/0298152 A1 | 12/2007 | De Baets | |
| 2011/0061645 A1* | 3/2011 | Fosdick | ................ C13K 1/06 127/30 |
| 2013/0189746 A1 | 7/2013 | Bertelsen et al. | |
| 2016/0273008 A1 | 9/2016 | Toyota et al. | |
| 2016/0278421 A1 | 9/2016 | Berrocal et al. | |

FOREIGN PATENT DOCUMENTS

| | | | | |
|---|---|---|---|---|
| JP | H02286078 A | 11/1990 | | |
| JP | H03117465 A | 5/1991 | | |
| JP | H03183454 A | 8/1991 | | |
| JP | H04103593 A | 4/1992 | | |
| JP | H04187093 A | 7/1992 | | |
| JP | H06228180 A | 8/1994 | | |
| JP | H07278170 A | * | 10/1995 | ............... C07H 3/06 |
| JP | H09224665 A | 9/1997 | | |
| JP | H10165192 A | 6/1998 | | |
| JP | 2000217546 A | 8/2000 | | |
| JP | 2013530719 A | 8/2013 | | |
| WO | 2012010597 A1 | 1/2012 | | |

OTHER PUBLICATIONS

Belloir, C., Neiers, F., & Briand, L. (2017). Sweeteners and sweetness enhancers. Current Opinion in Clinical Nutrition and Metabolic Care, 20(4), 279-285. (Year: 2017).*

* cited by examiner

*Primary Examiner* — Dale R Miller
(74) *Attorney, Agent, or Firm* — Fredrikson & Byron, P.A.

(57) ABSTRACT

The present invention relates to a non-digestible prebiotic oligosaccharide modified so as to incorporate one or more monosaccharide units thereon and have a higher sweetness value than the unmodified oligosaccharide. Uses and methods of producing the non-digestible prebiotic oligosaccharides are also described.

18 Claims, 4 Drawing Sheets

PREBIOTIC COMPOSITIONS AND METHODS OF PRODUCTION THEREOF

TECHNICAL FIELD OF THE INVENTION

The invention relates to sweet non-digestible oligosaccharides which have particular applications as functional food ingredients for foodstuffs and incorporation in meal replacement products and can be used by themselves to sweeten.

BACKGROUND TO THE INVENTION

Prebiotics are substrates that are selectively utilized by host microorganisms, such as lactobacilli or bifidobacteria, conferring a health benefit, and are finding much increased application into the food sector. Prebiotics can be non-digestible food ingredients that are selectively metabolised by colonic bacteria which contribute to improved health. As such, their use can promote beneficial changes within the indigenous gut microbial milieu and they can help survivability of probiotics. They are distinct from most dietary fibres like pectin, celluloses, xylan, which have a global effect on gut bacterial populations and are not selectively metabolised in the gut. Criteria for classification as a prebiotic is that it must resist gastric acidity, hydrolysis by mammalian enzymes and absorption in the upper gastrointestinal tract, and reach the colon in appropriate amount to be fermented by intestinal microbiota and selectively stimulate the growth and/or activity of intestinal bacteria associated with health and well-being.

It is an object of the present invention to provide non-digestible oligosaccharides which have an increased sweetness value. In particular, it is an object of the present invention to provide non-digestible oligosaccharides having an increased sweetness value, with low bitter and/or an undesirable after tastes. It is a further object of the present invention to provide sweeter and naturally derived fibres which are not digested in the human or animal gut and can therefore be used as a low calorie functional ingredient which can improve microbiome diversity.

SUMMARY OF THE INVENTION

In accordance with a first aspect of the present invention, there is provided a non-digestible oligosaccharide modified so as to incorporate one or more monosaccharides units thereon and have a higher sweetness value than the unmodified oligosaccharide.

In accordance with a related aspect of the present invention, there is provided a synthetic non-digestible oligosaccharide modified so as to incorporate one or more monosaccharides units thereon and have a higher sweetness value than the unmodified oligosaccharide.

In accordance with a further related aspect of the present invention, there is provided a prebiotic comprising a non-digestible oligosaccharide modified so as to incorporate one or more monosaccharides units thereon and have a higher sweetness value than the unmodified prebiotic oligosaccharide.

In accordance with a yet further related aspect of the present invention, there is provided a prebiotic composition comprising a synthetic non-digestible prebiotic oligosaccharide modified so as to incorporate one or more monosaccharides units thereon and have a higher sweetness value than the unmodified prebiotic oligosaccharide.

In the related aspects of the present invention, the invention may lie in the provision of a non-digestible oligosaccharide, which may or may not be (or be used as) a prebiotic.

The term "synthetic" and "synthesised" are intended to mean products which are not naturally occurring or produced in nature. The terms do of course encompass products which are 'man made' using natural products, such as naturally derived pre-cursor compositions and naturally derived enzymes.

The oligosaccharide of all related aspects may be modified during synthesis. Preferably, the oligosaccharide is synthesized using a disaccharide or oligosaccharide precursor and a different monosaccharide.

The present inventors have surprisingly found during the synthesis of non-digestible oligosaccharides, by incorporating different monosaccharides, they are able to increase the sweetness of the oligosaccharide without apparently disrupting the other functional aspects of the oligosaccharides.

The terms "modify", "modification" or "modified" are intended to mean to make a partial or minor change to the overall structure of the oligosaccharide without substantially altering the functional aspects of the oligosaccharide. The terms are also intended to encompass making partial or minor changes during synthesis, but could also encompass changes made post-synthesis.

The oligosaccharide of all related aspects may be selected from one or more of the following: inulin, fructooligosaccharides (FOS), galactooligosaccharides (GOS), α-galactooligosaccharides and β-glucooligosaccharides. Preferably, the oligosaccharide is selected from fructooligosaccharides (FOS) or galactooligosaccharides (GOS). Most preferably, the oligosaccharide is galactooligosaccharides (GOS).

The oligosaccharide of all related aspects has been modified by using a galactosidase or a glycosidase in the presence of different monosaccharides unit acceptor during synthesis. The oligosaccharide may have been fructosylated using β-galactosidase in the presence of a monosacharide acceptor. Preferably, the monosaccharide acceptor is fructose and the oligosaccharide has been modified by fructosylation.

It will be apparent to the skilled addressee that the β-galactosidase may be derived from a number of different species. It is however preferred that the β-galactosidase is derived from the *Aspergillus* genus. The *Aspergillus* species may be selected from one or more of the following: *Aspergillus officinalis*; *Aspergillus aculeatus*; *Aspergillus awamori*; *Aspergillus carbonarius*; *Aspergillus cellulosae*; *Aspergillus oryzae*; *Aspergillus flavus*; *Aspergillus japonicas*; *Aspergillus nidulansl*; or *Aspergillus niger*.

The oligosaccharide may be used for a number of applications, such as for use as a prebiotic. The oligosaccharide may be for incorporation in, or on, a food stuff, a food supplement or a calorie restricted meal replacement product. The oligosaccharide may also be used to replace part, the majority, or all, of the bulk sugar content in a foodstuff or used by itself as a sweetener. Advantageously, the inventors of the present invention have found that the oligosaccharides have a clean flavour profile, a low glycaemic index, which may be classified as fibres and help to maintain gut microbiome diversity and enhancement of health positive bacteria. The oligosaccharide may be in a granular or powdered form.

The term "foodstuff" is intended to mean any material which can be safely ingested by a human or animal, including, but not limited to foods, beverages, cereals, bakery products, breaded and battered products, dairy products, confectionary, snacks, and meals. The term includes those products which require reconstitution prior to being cooked or eaten. The term also includes any food/nutritional supplements or medicaments (such as vitamin tablets or antibiotic liquids).

It will be apparent to the skilled addressee that the oligosaccharides may be incorporated into a product, by way of blending or mixing the oligosaccharides with other ingredients. Alternatively, the oligosaccharides may be used to coat a product.

The oligosaccharide may be present with, or used in combination with unmodified oligosaccharides of the same type. During synthesis, at very high yields, the modified oligosaccharides may account for up to about 99% of the oligosaccharides. The combination may comprise up to about 95% modified oligosaccharides to unmodified oligosaccharides, or up to about 90% modified oligosaccharides to unmodified oligosaccharides, or up to about 80% modified oligosaccharides to unmodified oligosaccharides.

In accordance with a related second aspect of the invention, there is provided a combination of non-digestible oligosaccharides of the same type, wherein the combination comprises modified oligosaccharides and unmodified oligosaccharides, where the modified oligosaccharides are modified so as to incorporate one or more monosaccharide units and have a higher sweetness value than the unmodified oligosaccharides.

The modified oligosaccharides of the combination may comprise a non-digestible oligosaccharides as herein above described with reference to the first aspect.

The oligosaccharide may be for use as a prebiotic, or for incorporation in, or on, a food stuff, a food supplement or a calorie restricted meal replacement product.

In accordance with a third related aspect of the invention, there is provided a method for increasing the sweetness of non-digestible oligosaccharides, the method comprising modifying at least a portion of the oligosaccharides so as to incorporate one or more monosaccharide units thereon.

In the method, the oligosaccharide will preferably be modified so as to incorporate two or more monosaccharide units thereon.

In the method, the oligosaccharide may be selected from one or more of the following: inulin, fructooligosaccharides (FOS), galactooligosaccharides (GOS), α-galacto-oligosaccharides and β-glucooligosaccharidess. Preferably the oligosaccharide is selected from fructooligosaccharides (FOS) or galactooligosaccharides (GOS). Most preferably, the oligosaccharide is galactooligosaccharides (GOS).

The oligosaccharide may have been modified by using a galactosidase or a glycosidase in the presence of a monosaccharide unit acceptor during synthesis. The oligosaccharide may have been fructosylated using β-galactosidase in the presence of a monosaccharide acceptor.

As mentioned earlier, the β-galactosidase may be derived from the *Aspergillus* genus. The the β-galactosidase may be derived from one or more of the following species of *Aspergillus: Aspergillus officinalis; Aspergillus aculeatus; Aspergillus awamori; Aspergillus carbonarius; Aspergillus cellulosae; Aspergillus oryzae; Aspergillus flavus; Aspergillus japonicas; Aspergillus nidulansl;* or *Aspergillus niger.*

The monosaccharide acceptor may be fructose and the oligosaccharide has been modified by fructosylation. It will however be apparent that a range of novel sweet non-digestible oligosaccharides can be produced using different enzymes and monosaccharide acceptors.

In the method, the modified oligosaccharide may be produced with unmodified oligosaccharides of the same type. During production, the yield of the modified oligosaccharides may be up to about 99%. However, the yield could be lower depending upon synthesis conditions and may up to about 95%, up to about 90%, or up to about 80%.

All of the oligosaccharides as described herein above have been shown to advantageously form sweet natural and healthy fibres which are not digested in the human or animal gut and can therefore be used as calorie free, or substantially calorie free, functional ingredients. These sweet fibres have been developed as potential bulk sugar replacements as a product which has sweetness similar to sucrose but contain no, or substantially no, calories, whilst also improving microbiome diversity.

The oligosaccharides have surprisingly been found to be significantly sweeter than all other samples, with the advantage of low off-flavours (e.g. bitterness, sourness, staleness, saltiness etc.)

The present inventors have shown through experimentation that the prebiotic compositions provide for natural, low calorie, sweet healthy fibres with gut microbiome functionality as potential bulk sugar replacement in a wide range of food products.

In accordance with a fourth aspect of the present invention, there is provided the use of the prebiotic compositions as herein above described as a low calorie or calorie free sweet prebiotic. The use may also be as a bulk sugar replacement ingredient to replace all or a portion of a sugar or sucrose content of a foodstuff. It will be apparent to the skilled addressee that the composition may also be incorporated in a range of foodstuffs, food supplements or calorie restricted meal replacement products.

In accordance with a related fifth aspect of the present invention, there is provided a method for increasing the sweetness of non-digestible oligosaccharides, the method comprising modifying at least a portion of the oligosaccharides, during synthesis, so as to incorporate one or more monosaccharide units thereon.

The method for producing a modified non-digestible oligosaccharide, may comprise: mixing together a disaccharide precursor, a galactosidase or glycosidase and a monosaccharide acceptor under suitable conditions so as to enable the enzymatic production of non-digestible oligosaccharides with different monosaccharide units.

In the method of production, the non-digestible oligosaccharide precursor will be largely dependent upon which non-digestible oligosaccharide is to be produced. For example, the non-digestible oligosaccharide precursor may comprise lactose if GOS is to be produced. The galactosidase or glycosidase chosen will also be largely dependent upon to the non-digestible oligosaccharide to be produced. For example, the galactosidase or glycosidase may be β-galactosidase if GOS is to be produced. The monosaccharide acceptor may comprise a number of acceptors, for example fructose may be chosen if the GOS to be produced is a fructosylated GOS. It will be apparent to the skilled addressee that other non-digestible oligosaccharide precursors, other glycosidases such as β-glucosidase and dextransucrase may be employed. It will also be apparent that other donors, such as sucrose, raffinose, lactulose and other monosaccharides acceptors, may be used to produce novel modified non-digestible oligosaccharides having a sweeter value than unmodified non-digestible oligosaccharides of the same type.

It will be apparent to the skilled addressee that a number of the features of the oligosaccharides listed in respect to a number of the aspects of the invention will be interchangeable with the combinations and methods also described.

DETAILED DESCRIPTION OF THE INVENTION

Embodiments of the present invention will now be described, by way of examples only.

Figure 4:
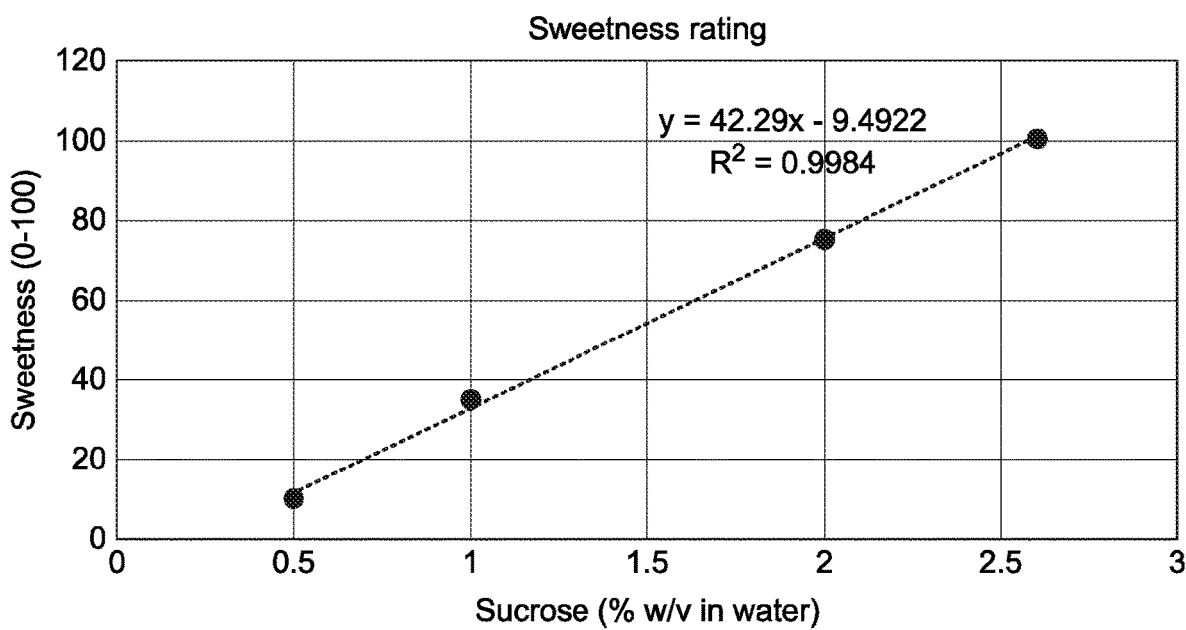
Figure 5A:
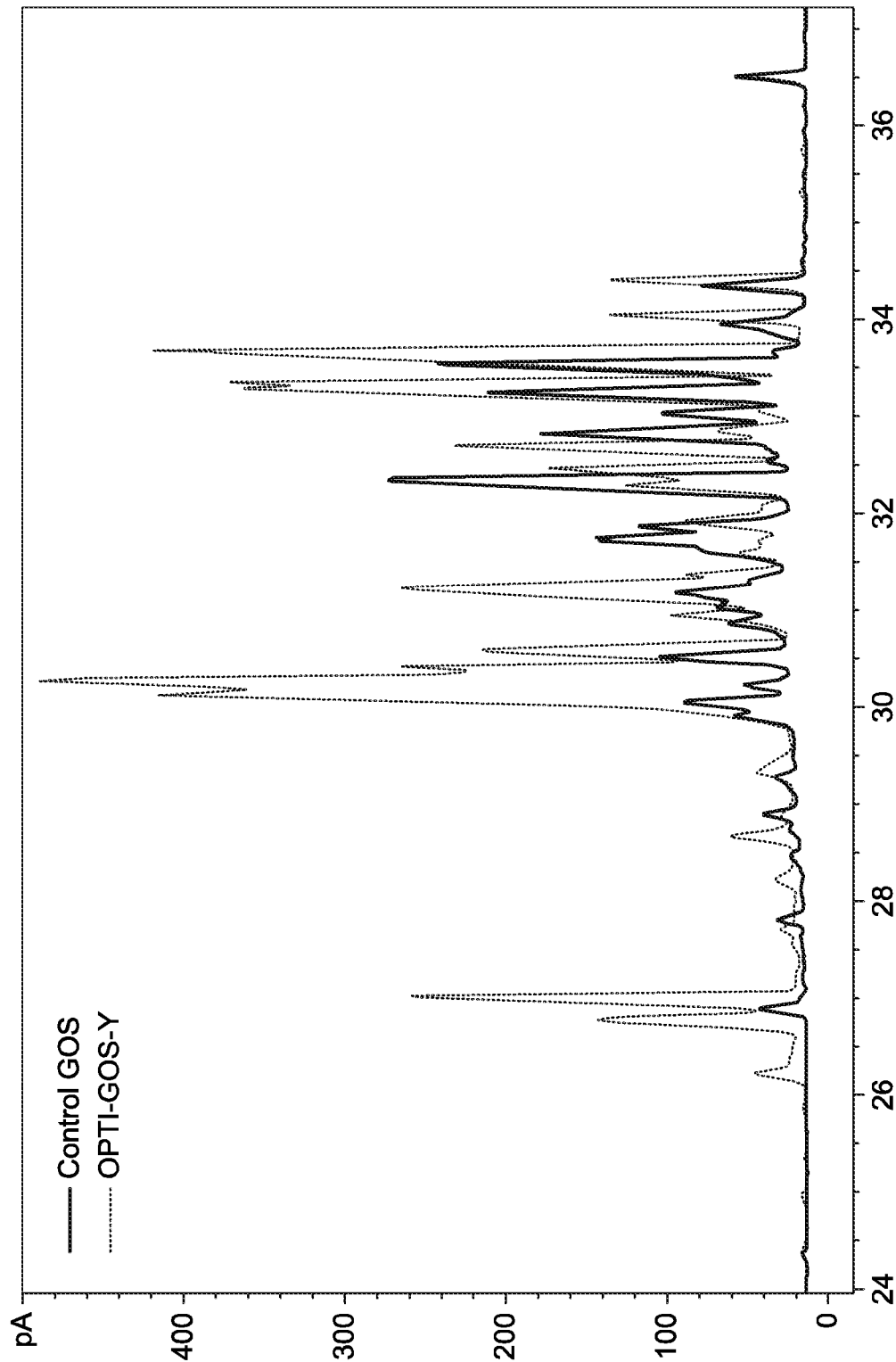
Figure 5B:
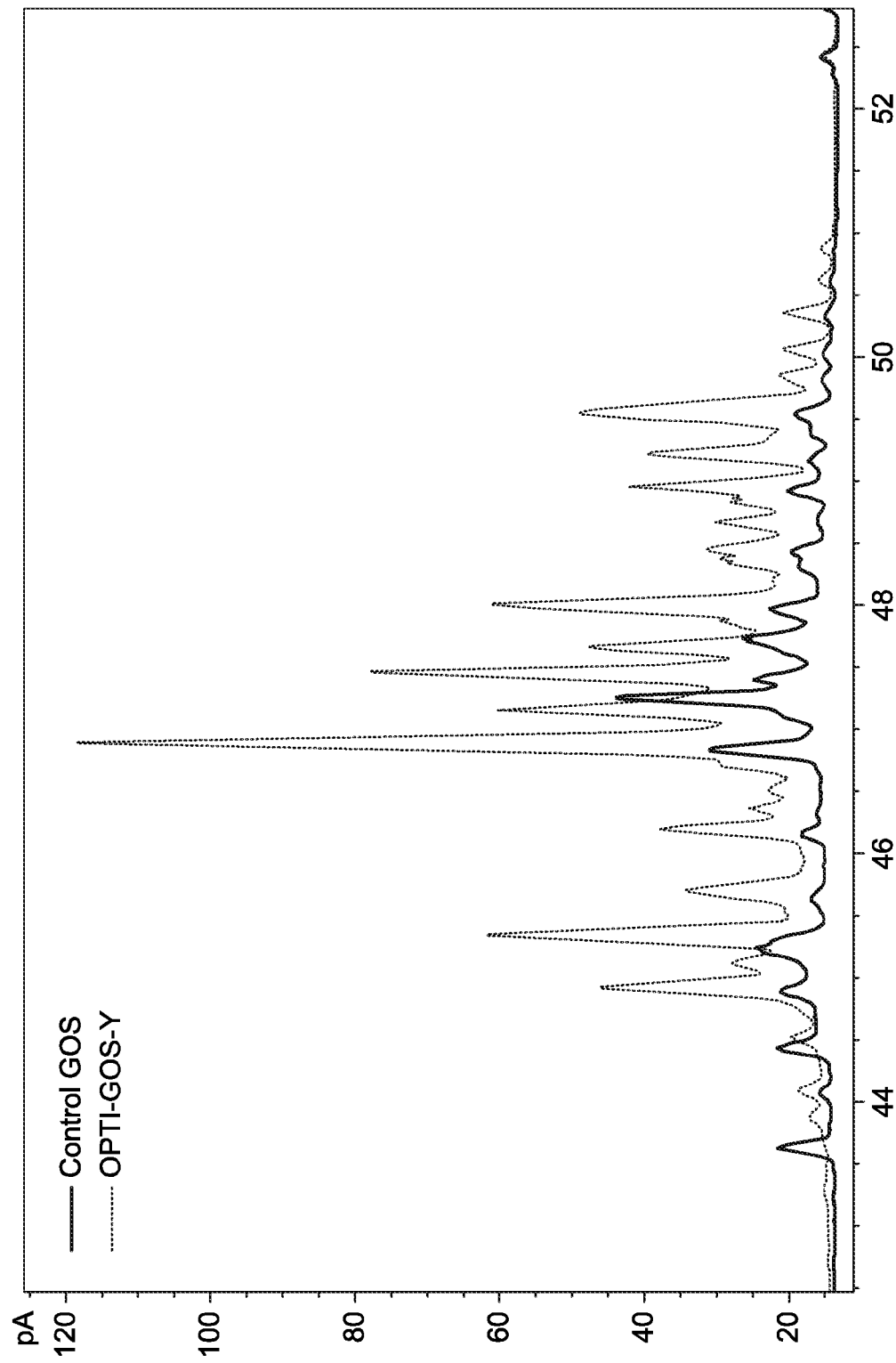

FIG. 4 is a plot graph showing the dose-response curve for the sweetness of the sucrose standards used in Example 1; and FIG. 5A shows the gas chromatography profile of the trimethylsilyl oximes of disaccharides fraction of the OPTI-GOS-Y tested in Example 1, whereas FIG. 5B the gas chromatography profile of the trimethylsilyl oximes of trii-saccharides fraction of the OPTI-GOS-Y tested in Example 1.

EXAMPLE 1—SENSORY PROFILING OF OLIGOSACCHARIDES

The aim of these experiments was to determine the intensity of sweetness and any off flavours of a number of oligosaccharides.

Preparation of Samples

The following commercial and experimental products were supplied by Optibiotix Health Ltd, York, UK to the Sensory Science Centre at the University of Reading, Department of Food and Nutritional Sciences: GOS 1; GOS 2; GOS 3; GOS 4; OPTI-GOS-Y; GOS from lactulose; lactose and lactulose.

All samples underwent microbiological clearance testing.

All materials were stored at ambient temperature. Sucrose was purchased as white granulated sugar (Sainsburys Plc, London, UK). Water was Harrogate Spa mineral water (Harrogate Water Brands, Harrogate, UK).

All oligosaccharides were prepared as a 5% w/v solution in mineral water. Weights were accurate to 3 decimal places, samples were made up in volumetric flasks. All samples dispersed well and solubilised easily in water. Sucrose samples were prepared at 0.5, 1.0, 2.0 and 2.6% w/v.

Sensory Profiling Method

The trained sensory panel at the Sensory Science Centre were employed for sensory profiling of the samples. There were 11 panellists with between 6 months and 9 years' experience. A QDA (quantitative descriptive analysis) profiling approach was taken. The panel were retrained at the start of the sample set. This re-training focused on ensuring that they could reliably score sweetness relative to the new concentration of sucrose standard positions.

Rating was carried out independently using unstructured lines scales (scaled 0-100), in duplicate, in isolated sensory booths. However, in order to improve discrimination for sweetness, the four sucrose samples were used as standards and the mean values for each of these samples, as agreed by the panel, are shown in Table 1 below.

TABLE 1

(Means scores (scale 0-100) for 4 sucrose reference samples)

| Standard Number | Sucrose Concentration (% w/v) | Mean Rating (0-100) |
| --- | --- | --- |
| 1 | 0.5 | 10 |
| 2 | 1.0 | 35 |
| 3 | 2.0 | 75 |
| 4 | 2.6 | 100 |

At the start of each scoring session the panel tasted the four reference samples in order of increasing strength to re-familiarise themselves with the positioning of these levels of sweetness on the line scale. The reference samples (10 ml) were served in transparent polystyrene cups (30 ml). They then palate cleansed with warm filtered tap water and low salt crackers (Carr's water crackers) before commencing the sample tasting session, and again between each sample scoring session.

Samples, labelled with random 3 digit codes, were presented in a balanced presentation order in a monadic sequential manner, 4 samples were tasted per session. Samples were served at 23-24° C. (room temperature) with air conditioning of the room set to 23° C.

The panel used 16 attributes to define the oligosaccharide samples, as shown in Table 2 below.

TABLE 2

(Means scores (0-100) for oligosaccharides (Note: [abcdef]superscripts of the same letter indicate no significant difference found at $p \leq 0.05$))

| | GOS 1 | GOS 2 | OPTI-GOS-Y | GOS FROM LACTULOSE | LACTOSE | LACTULOSE | GOS 3 | GOS 4 | Fisher's LSD Value | Sample Significant (p) |
| --- | --- | --- | --- | --- | --- | --- | --- | --- | --- | --- |
| Sweet | 28.1 c | 37.3 c | 75.8 a | 33.7 c | 49.5 b | 56.4 b | 53.0 b | 51.3 b | 11.5 | <0.0001 |
| StrengthOffFlavour | 25.3 bc | 19.8 c | 26.8 bc | 49.5 a | 26.5 bc | 26.4 bc | 24.3 c | 35.6 b | 9.8 | <0.0001 |
| Bitter | 4.6 bc | 5.9 bc | 2.5 c | 12.7 a | 7.5 b | 2.9 c | 4.2 bc | 5.8 bc | 4.3 | 0.0001 |
| Cardboard_/_Stale | 10.8 ab | 4.5 bc | 2.9 c | 12.9 a | 9.0 abc | 5.1 bc | 6.2 bc | 4.1 bc | 6.6 | 0.0283 |
| CandyFloss | 2.3 bc | 2.3 bc | 18.0 a | 1.1 c | 3.7 bc | 9.3 b | 5.8 bc | 4.3 bc | 7.9 | 0.0005 |
| Sour/Dairy/Rancid | 4.7 ab | 2.1 b | 2.0 b | 10.0 a | 6.9 ab | 4.9 ab | 5.8 ab | 7.9 ab | 5.9 | 0.0933 |
| Metallic | 3.2 b | 1.0 b | 1.6 b | 10.2 a | 3.5 b | 2.7 b | 1.3 b | 2.3 b | 3.2 | <0.0001 |
| Salty | 3.1 | 1.6 | 3.1 | 4.9 | 2.5 | 2.4 | 2.2 | 2.9 | 2.1 | 0.1082 |
| CrustyBread | 0.0 | 0.9 | 0.1 | 0.0 | 0.6 | 0.0 | 0.4 | 0.0 | 1.0 | 0.4938 |
| Perfume | 1.3 b | 0.1 b | 1.4 b | 4.8 a | 0.0 b | 1.0 b | 0.7 b | 3.4 ab | 3.2 | 0.0468 |
| Sweet After Taste | 22.1 c | 23.5 bc | 49.9 a | 22.2 c | 30.6 bc | 33.4 b | 32.8 b | 26.7 bc | 10.6 | <0.0001 |

Panellists were given 5 ml of each sample to taste. The 5 ml was measured out by plastic syringe into the clear tasting cups (30 ml). The panellists ensured that they carefully sipped the sample and let it flow over the top of their tongue before swallowing. The sipped half of the sample into their mouth to score the first 6 attributes and the second half to score the following 6 attributes. After effects were scored after a 30 second time delay.

Data Analysis

Data were analysed using a mixed model ANOVA where panellists were treated as random effects and samples as fixed effects, the main effects were tested against the sample by assessor interaction. Multiple pairwise comparisons were carried out using Fishers LSD and a significant difference was declared at an alpha risk of 5% ($p \leq 0.05$). Data analysis was carried out using Senpaq software (Qi Statistics, Reading, UK).

Sensory Profiling Results

Figure 1:
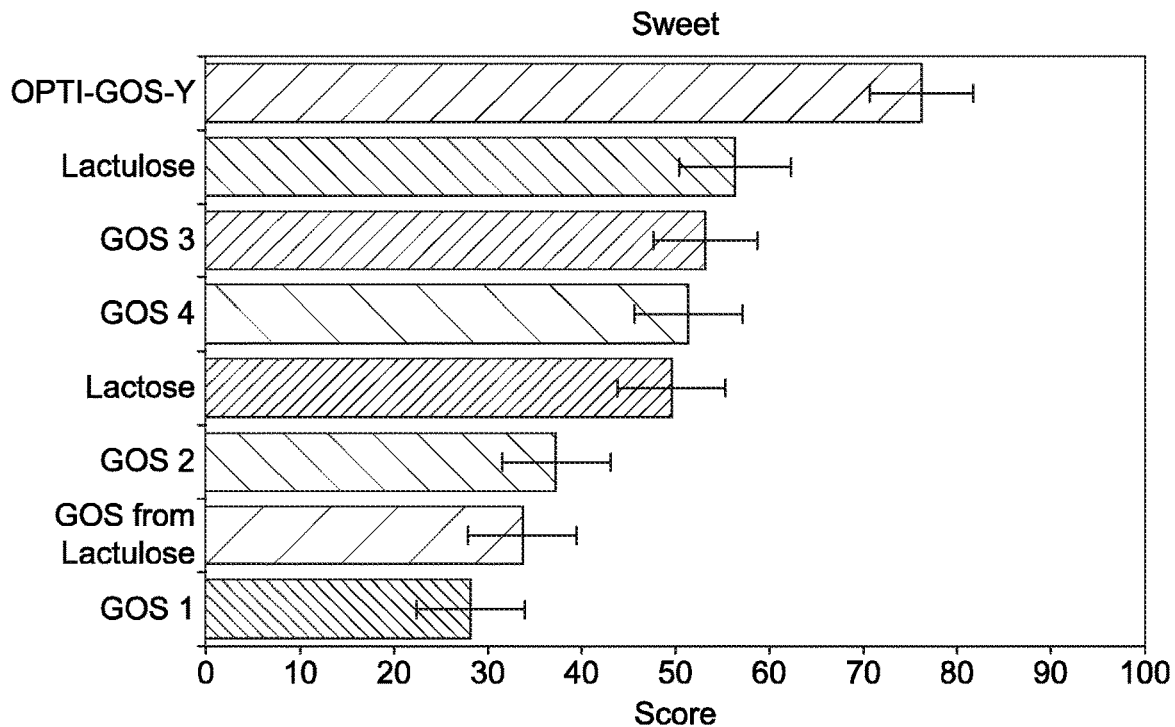
FIG. 1 is a bar chart showing the key attributes found to be significantly different between samples of Example 1 for a sweet taste (bars represent mean values, error bars extend +/−half LSD)
Figure 2:
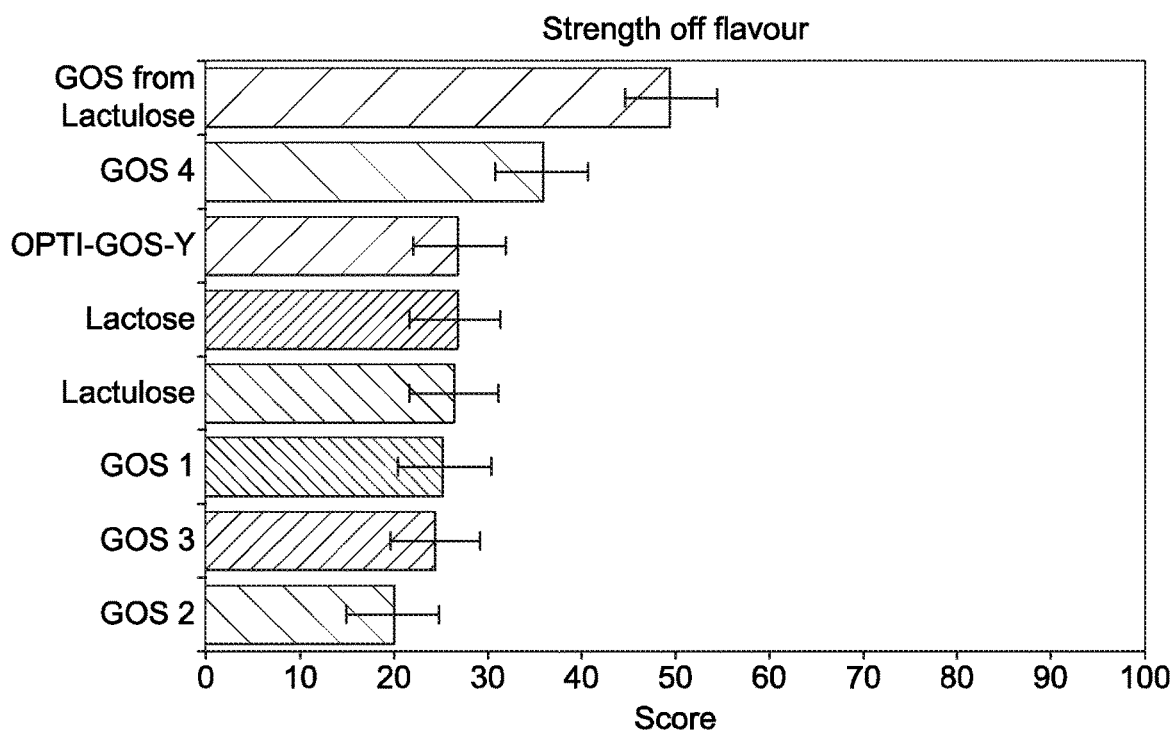
FIG. 2 is a bar chart showing the key attributes found to be significantly different between samples of Example 1 for off flavours (bars represent mean values, error bars extend +/−half LSD)
Figure 3:
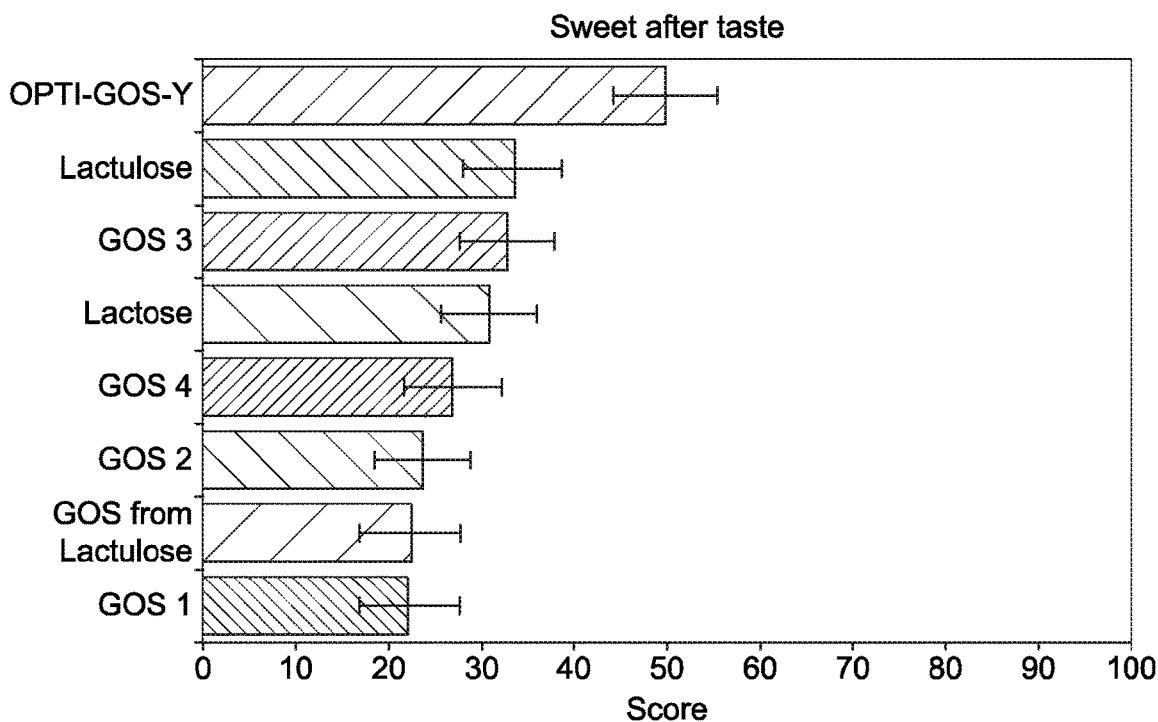
FIG. 3 is a bar chart showing the key attributes found to be significantly different between samples of Example 1 for a sweet after taste (bars represent mean values, error bars extend +/−half LSD)

Of the 11 attributes rated, 8 were significantly different between samples (as illustrated in Table 2 above). The most substantial differences were in sweet taste, strength of off-flavour and sweet after taste (see FIGS. 1 to 3). The OPTI-GOS-Y (fructose derived galactooligosaccharide, synthesised in CIAL (CSIC UAM) Madrid, 5% w/v) was significantly sweeter than all other samples. It had a mean sweetness of 76 which was equivalent to the 2% sucrose (w/v) standard. The least sweet samples were the GOS 1, GOS 2 and GOS from lactulose (synthesised by CIAL (CSIC-UAM) Madrid).

The sample with the strongest off flavour was the GOS from lactulose; the off flavour was due to bitter taste, cardboard/stale flavour, sour/rancid notes and metallic taste as shown in Table 2. The OPTI-GOS-Y sample had significantly lower overall strength of off flavour, and the off flavour in this sample was due to different notes, the only other attribute that it was substantially and significantly high in was the candy floss flavour.

Although the sucrose standards were not rated in a blinded manner, it is useful to compare the mean sweetness values samples to the sweetness values of the 4 sucrose standards. FIG. 4 shows the dose-response curve for the sweetness of the sucrose standards. Within the range of concentrations use the relationship was linear and the linear regression equation was: Sweetness=15.5(sucrose)−22.5 (R-square=0.99).

Using this regression equation the sweetness values of the samples have been converted to equivalent sucrose (ES) concentrations. This has been done for the mean sweetness rating as well as for the values plus and minus the standard deviation. In order to calculate the relative sweetness (RS) values the following equation was used:

RS=1/(5/ES)×100.

The values of ES and RS are given in Table 3 below.

TABLE 3

Equivalent Sucrose and Relative Sweetness Values
([a] www.sugar-and-sweetener-guide.com/sweetener-values.html).

| Sample | Equivalent Sucrose (%) to 5% saccharide | | | Relative Sweetness (sucrose = 100) (RS) | | |
|---|---|---|---|---|---|---|
| | Mean | Min | Max | Mean | Min | Max |
| GOS 1 | 0.9 | 0.6 | 1.2 | 18 | 12 | 24 |
| GOS 2 | 1.1 | 0.7 | 1.5 | 22 | 14 | 30 |

TABLE 3-continued

Equivalent Sucrose and Relative Sweetness Values
([a] www.sugar-and-sweetener-guide.com/sweetener-values.html).

| Sample | Equivalent Sucrose (%) to 5% saccharide | | | Relative Sweetness (sucrose = 100) (RS) | | |
|---|---|---|---|---|---|---|
| | Mean | Min | Max | Mean | Min | Max |
| OPTI-GOS-Y | 2.0 | 1.5 | 2.6 | 40 | 29 | 51 |
| GOS FROM LACTULOSE | 1.0 | 0.7 | 1.3 | 20 | 14 | 27 |
| LACTOSE | 1.4 | 0.9 | 1.9 | 28 | 18 | 38 |
| LACTULOSE | 1.6 | 1.1 | 2.0 | 31 | 22 | 40 |
| GOS 3 | 1.5 | 0.9 | 2.0 | 30 | 19 | 40 |
| GOS 4 | 1.4 | 1.1 | 1.8 | 29 | 22 | 35 |

The 5% oligosaccharides were all equivalent (on average) to between 0.9% and 2% sucrose, leading to relative sweetness values between 18 and 40. These values are not completely in line with the literature available for lactose (literature RS 15, calculated RS between 18 and 38). However, it must be noted that the sensory panel were rating on just 0.5 ml sample.

In conclusion, significant differences in sweet taste were found for the oligosaccharides tested in this study. All oligosaccharides were prepared in mineral water at 5% w/v and rated for sweetness along a structured scale anchored by references of 0.5, 1.0, 2.0 and 2.6% w/v sucrose. The sweetness of the 5% w/v oligosaccharide samples varied from 0.9 to 2% sucrose. The fructose derived galactooligosaccharide was significantly sweeter than all other samples and was low in all off-flavours rated other than candy-floss flavour.

Optimisation of OPTI-GOS-Y (GOS Mixed with GOS-Fructosylated)

This experiment sought to investigate the potential yield and preferred enzymes for producing, as a prebiotic, a mixture of GOS (approx. 30%) and GOS-fructosylated (approx. 5%). The three commercial enzymes which were investigated were β-galactosidase from a range of microbial species including *Aspergillus*. The substrate used was a range of ratios of Lactose and Fructose. Purification was performed using yeast fermentation and the drying process used lyophilisation and rotovapor.

FIG. 5A shows the disaccharide fraction, whereas FIG. 5B shows the trisaccharide fraction.

The best results were obtained with β-galactosidase from *Aspergillus* where it showed higher yields. It is believed that this is the first report of GOS fructosylated as prebiotic sweetener. The sweet value is higher compared to other commercial GOS (the product has a sweetness value of 75 compared with sucrose (100)).

Impact of OPTI-GOS on Metabolic Activity

The impact of Opti-GOS (1% w/v) on the metabolic activity of the human gut microbiome was investigated in pH and temperature-controlled batch cultures. Impact of opti-GOS on the concentration of organic acids was compared to short chain fructooligosaccharides (FUJIFILM Wako Chemicals, Germany), and a carbohydrate negative control. Galactooligosaccharides produced by the activity the same enzymes used for the synthesis of Opti-GOS were also tested.

Freshly voided faecal samples were obtained from five healthy adults, free from gastrointestinal disorders who had not taken antibiotics for 6 months prior to the study and prebiotics and/or probiotics for 6 weeks prior to the study.

Sterile fermenters (20 mL working volume, Soham scientific, Ely, UK) were filled with pre-reduced sterile basal media consisting of: peptone water (Oxoid, Basingstoke, UK) 2 g $L^{-1}$; yeast extract (Oxoid, Basingstoke, UK) 2 g $L^{-1}$; NaCl 0.1 g $L^{-1}$; $K_2HPO_4$ 0.04 g $L^{-1}$; $KH_2PO_4$ 0.04 g $L^{-1}$; $MgSO_4.7H_2O$ 0.01 g $L^{-1}$; $CaCl_2.6H_2O$ 0.01 g $L^{-1}$; $NaHCO_3$ 2 g $L^{-1}$; haemin 0.05 g $L^{-1}$; cysteine·HCl 0.5 g $L^{-1}$; bile salts 0.5 g $L^{-1}$, vitamin K1 10 µL; Tween 80 2 mL (Sigma Aldrich) and sparged with oxygen-free $N_2$ to establish and maintain anaerobic conditions. Stirring was achieved using magnetic stirrers. Test carbohydrates (1% w/v) were added in designated vessels just prior to inoculation with the faecal slurry from a single donor (10% v/v prepared in anaerobic phosphate buffered saline). All tests for a single donor were carried out in parallel. Fermentation temperature was maintained at 37° C. by means of a circulating water bath. Automated pH controllers (Fermac 260; Electrolab UK) kept culture pH within a range of 6.7 and 6.9 by adding 0.5 M NaOH and 0.5 M HCl as required. Fermentations were run for a period of 24 h and samples were withdrawn at 0, 5, 10, and 24 h for organic acid analysis.

Organic acid (OA) concentrations were determined by gas chromatography equipped with flame ionisation detector (GC-FID) based on the method described by Richardson et al (1989) using 2-ethyl butyric acid as an internal standard. A gas chromatograph analyser (Agilent/HP 6890) equipped with a Flame Ionization Detector (FID) and an HP-5MS column (30 m×0.25 mm) with a 0.25 µm coating (Crosslinked (5%-Phenyl)-methylpolysiloxane, Hewlett Packard, UK) was used for SCFA measurements. Helium was used as carrier gas at a flow rate of 1.7 mL/min (head pressure 133 KPa). Oven initial temperature was set at 63° C., followed by a temperature ramp of 15° C./min to 190° C. and held constant for 3 minutes. A split ratio of 100:1 was used. The appearance of OA in the chromatograms was confirmed based on the retention times of the respective commercial OA standards (Lactic acid, Acetic acid, Propionic acid and Butyric acid) (Sigma-Aldrich, UK).

Opti-GOS was found to mediate significantly higher levels of acetate compared to baseline from 5 h of fermentation. Acetate concentrations were significantly higher compared to the negative control at each time points and were similar to those of the prebiotic positive control and GOS (as shown in Table 4 below).

Propionate concentrations were significantly higher compared to the negative control at 10 and 24 h of fermentation and were similar to the levels observed by GOS and the positive control.

Similarly, butyrate increased from 5 h of fermentation, being significantly higher compared to the negative control and showed similar patterns to that of the prebiotic control and GOS.

Lactate significantly increased at 5 and 10 h of fermentation at levels significantly higher compared to the negative control following similar patterns to the prebiotic control and GOS. Lactate is a fermentation intermediate, that is rapidly utilised through cross-feeding by other members of the gut microbiome. Lactate accumulates in culture when the rate of production is higher compared to the rate of utilisation and it is characteristic of rapid gut microbiome fermentation rates observed during the saccharolysis of oligosaccharides. This indicates that opti-GOS is fermented rapidly, following a behaviour that is well established for other prebiotic oligosaccharides, such as FOS and GOS.

Overall the metabolic activity of the gut microbiome when fermenting opti-GOS was similar to that of the prebiotic positive control (FOS) and GOS in terms both of fermentation kinetics but also of specific organic acid production. Opti-GOS behaved similarly to commercially available prebiotics, with their impact on the metabolic activity of the human gut microbiome being characteristic of oligosaccharide saccharolysis. They all increased significantly acetate but also propionate and butyrate, organic acids with important role in cholesterolgenesis, appetite regulation, tight junction integrity and immunomodulation.

TABLE 4

(short-chain fatty acids and lactate concentration after 5, 10 and 24 h of fermentation with human faecal samples)

| Organic acids | Time point (h) | SFCA Concentration (mM) | | | |
|---|---|---|---|---|---|
| | | Negative Control | Positive Control | GOS CONTROL | OPTI-GOS |
| ACETATE | 0 | 0.73 ± 0.01 | 0.73 ± 0.01 | 0.73 ± 0.01 | 0.73 ± 0.01 |
| | 5 | 4.05 ± 0.30$^a$ | 19.83 ± 1.57$^b$ | 24.51 ± 0.12$^b$ | 20.34 ± 0.32$^b$ |
| | 10 | 8.15 ± 0.35$^a$ | 43.89 ± 0.10$^b$ | 43.09 ± 0.30$^b$ | 32.82 ± 0.09$^b$ |
| | 24 | 12.99 ± 0.16$^a$ | 43.60 ± 0.17$^b$ | 56.11 ± 0.24$^b$ | 45.19 ± 0.01$^b$ |
| PROPIONATE | 0 | 0.15 ± 0.00 | 0.15 ± 0.00 | 0.15 ± 0.00 | 0.15 ± 0.00 |
| | 5 | 1.39 ± 0.07$^a$ | 2.30 ± 0.29$^{ab}$ | 3.17 ± 0.02$^{ab}$ | 3.55 ± 0.14$^b$ |
| | 10 | 1.86 ± 0.12$^a$ | 5.84 ± 0.01$^b$ | 4.85 ± 0.07$^b$ | 6.57 ± 0.00$^b$ |
| | 24 | 2.53 ± 0.10$^a$ | 6.78 ± 3.50$^{ab}$ | 11.89 ± 0.27$^b$ | 11.19 ± 0.09$^b$ |
| BUTYRATE | 0 | 0.11 ± 0.00 | 0.11 ± 0.00 | 0.11 ± 0.00 | 0.11 ± 0.00 |
| | 5 | 0.45 ± 0.00$^a$ | 0.69 ± 0.17$^{ab}$ | 1.04 ± 0.05$^b$ | 1.17 ± 0.06$^b$ |
| | 10 | 1.36 ± 0.01$^a$ | 2.89 ± 0.01$^{ab}$ | 4.74 ± 0.03$^b$ | 4.61 ± 0.00$^{ab}$ |
| | 24 | 2.45 ± 0.00$^a$ | 6.56 ± 0.69$^{ab}$ | 13.10 ± 0.05$^c$ | 8.27 ± 0.08$^{bc}$ |
| LACTATE | 0 | 0.11 ± 0.00 | 0.11 ± 0.00 | 0.11 ± 0.00 | 0.11 ± 0.00 |
| | 5 | 0.12 ± 0.00$^a$ | 8.95 ± 1.07$^b$ | 10.29 ± 0.11$^b$ | 9.88 ± 0.38$^b$ |
| | 10 | 0.03 ± 0.00$^a$ | 20.90 ± 0.19$^c$ | 15.35 ± 0.34$^c$ | 8.20 ± 0.00$^b$ |
| | 24 | 0.00 ± 0.00$^a$ | 3.75 ± 5.30$^a$ | 5.93 ± 0.10$^a$ | 1.86 ± 0.16$^a$ |
| TOTAL | 0 | 1.15 ± 0.25 | 1.15 ± 0.25 | 1.15 ± 0.25 | 1.15 ± 0.25 |
| | 5 | 6.22 ± 1.47$^a$ | 31.90 ± 7.46$^a$ | 39.26 ± 9.10$^a$ | 35.18 ± 7.62$^a$ |
| | 10 | 12.03 ± 2.92$^a$ | 73.92 ± 16.46$^c$ | 68.65 ± 15.63$^{bc}$ | 52.81 ± 11.63$^b$ |
| | 24 | 20.55 ± 4.54$^a$ | 82.23 ± 15.85$^b$ | 91.12 ± 19.66$^b$ | 70.58 ± 15.99$^b$ |
| ACETATE/ PROPIONATE RATIO | 0 | 4.77 | 4.77 | 4.77 | 4.77 |
| | 5 | 2.90 | 8.63 | 7.72 | 5.74 |
| | 10 | 4.38 | 7.51 | 8.88 | 5.00 |
| | 24 | 5.14 | 1.97 | 4.72 | 4.04 |

The forgoing embodiments are not intended to limit the scope of the protection afforded by the claims, but rather to describe examples of how the invention may be put into practice.

The invention claimed is:

1. A prebiotic comprising one or more non-digestible oligosaccharide(s), wherein at least one of the one or more non-digestible oligosaccharide(s) is modified so as to incorporate one or more monosaccharides such that the modified one or more non-digestible oligosaccharide(s) has a higher sweetness value than the unmodified one or more non-digestible oligosaccharide(s) from which the modified one or more non-digestible oligosaccharide(s) is derived, wherein the one or more non-digestible oligosaccharide(s) comprises fructose-modified galactooligosaccharide (GOS), optionally further modified with monosaccharides other than fructose; and wherein the one or more modified non-digestible oligosaccharide(s) is in combination with the unmodified one or more non-digestible oligosaccharide(s) and the combination comprises up to about 95% of the modified one or more non-digestible oligosaccharide(s), with the remainder of the combination comprising the unmodified one or more non-digestible oligosaccharide(s).

2. The prebiotic as claimed in claim 1, wherein the one or more non-digestible oligosaccharide(s) is modified during synthesis.

3. The prebiotic as claimed in claim 2, wherein the one or more non-digestible oligosaccharide(s) is synthesized by a reaction between a disaccharide or oligosaccharide precursor and a monosaccharide acceptor.

4. The prebiotic as claimed in claim 1, wherein the one or more non-digestible oligosaccharide(s) is modified with two or more monosaccharides.

5. The prebiotic as claimed in claim 1, further comprising one or more of the following: inulin, fructooligosaccharides (FOS), α-galactooligosaccharides and β-glucooligosaccharides.

6. The prebiotic as claimed in claim 1, wherein the modified one or more non-digestible oligosaccharide(s) is modified by using a galactosidase or a glycosidase in the presence of a monosaccharide acceptor during synthesis.

7. The prebiotic as claimed in claim 6, wherein the modified one or more non-digestible oligosaccharide(s) is fructosylated using β-galactosidase in the presence of a monosaccharide acceptor.

8. The prebiotic as claimed in claim 7, wherein the monosaccharide acceptor is fructose.

9. The prebiotic as claimed in claim 7, wherein the β-galactosidase is derived from the *Aspergillus* genus.

10. The prebiotic as claimed in claim 1, in a granular or powdered form.

11. The prebiotic as claimed in claim 1, for incorporation in, or on, a food stuff, a food supplement or a calorie restricted meal replacement or as a sweetener.

12. A combination of non-digestible prebiotic oligosaccharides, wherein the combination comprises modified oligosaccharides and unmodified oligosaccharides, where the modified oligosaccharides are modified during synthesis so as to incorporate one or more monosaccharides such that the modified oligosaccharides have a higher sweetness value than the unmodified oligosaccharides, from which the modified oligosaccharides are derived, wherein the modified oligosaccharides comprise galactooligosaccharides (GOS) which has been modified by fructosylation, and wherein the combination comprises up to about 95% of the modified oligosaccharides with the remainder of the combination comprising the unmodified oligosaccharides.

13. A method for increasing the sweetness of one or more non-digestible oligosaccharide(s), the method comprising modifying at least one of the one or more non-digestible oligosaccharide(s), during synthesis, so as to incorporate one or more monosaccharides such that the modified one or more non-digestible oligosaccharide(s) has a higher sweetness value than the unmodified one or more non-digestible oligosaccharide from which the modified one or more non-digestible oligosaccharide(s) is derived, wherein the one or more non-digestible oligosaccharide(s) comprises fructose-modified galactooligosaccharide (GOS), optionally further modified with monosaccharides other than fructose; and wherein the one or more modified non-digestible oligosaccharide(s) is in combination with the unmodified one or more non-digestible oligosaccharide(s) and the combination comprises up to about 95% of the modified one or more non digestible oligosaccharide(s), with the remainder of the combination comprising the unmodified one or more non-digestible oligosaccharide(s).

14. The method as claimed in claim 13, wherein the modified one or more non-digestible oligosaccharide(s) is modified with two or more monosaccharides.

15. The method as claimed in claim 13, wherein the modified one or more non-digestible oligosaccharide(s) is modified by using a galactosidase or a glycosidase in the presence of a monosaccharide acceptor during synthesis.

16. The method as claimed in claim 15, wherein the modified one or more non-digestible oligosaccharide(s) is fructosylated using β-galactosidase in the presence of a monosaccharide acceptor.

17. The method as claimed in claim 16, wherein the β-galactosidase is derived from *Aspergillus*.

18. The method as claimed in claim 16, wherein the monosaccharide acceptor is fructose.

* * * * *